US008236957B2

(12) United States Patent
Rezaie et al.

(10) Patent No.: US 8,236,957 B2
(45) Date of Patent: Aug. 7, 2012

(54) PROCESS FOR MAKING MORPHINAN-6α-OLS

(75) Inventors: Robert Rezaie, Blackstone Heights (AU); Timothy S. Bailey, Blackstone Heights (AU)

(73) Assignee: Janssen Pharmaceutica B.V. (BG)

( * ) Notice: Subject to any disclaimer, the term of this patent is extended or adjusted under 35 U.S.C. 154(b) by 437 days.

(21) Appl. No.: 12/538,545

(22) Filed: Aug. 10, 2009

(65) Prior Publication Data

US 2010/0036128 A1 Feb. 11, 2010

Related U.S. Application Data

(60) Provisional application No. 61/188,574, filed on Aug. 11, 2008.

(51) Int. Cl.
*C07D 489/02* (2006.01)
*C07D 489/08* (2006.01)
(52) U.S. Cl. .......................................... 546/44; 546/45
(58) Field of Classification Search .................. 546/44, 546/45
See application file for complete search history.

(56) References Cited

U.S. PATENT DOCUMENTS

| | | | |
|---|---|---|---|
| 3,830,819 | A | 8/1974 | Grew et al. |
| 5,208,338 | A | 5/1993 | de Costa et al. |
| 5,336,483 | A | 8/1994 | de Costa et al. |
| 5,756,745 | A | 5/1998 | Kavka et al. |
| 6,887,999 | B1 | 5/2005 | Likhotvorik et al. |

FOREIGN PATENT DOCUMENTS

| | | |
|---|---|---|
| WO | WO 2007/121114 | 10/2007 |
| WO | WO 2008/137672 | 11/2008 |

OTHER PUBLICATIONS

International Search Report PCT/AU2009/000925, Aug. 19, 2009.
Sargent, et al., "Hydroxylated Codeine Derivatives", Journal of Organic Chemistry, vol. 23, 1958 pp. 1247-1251.
Currie, et al. "Some Reactions of 14-Hydroxycodeine", Journal of Organic Chemistry, 1960, pp. 773-781.
Burke, et al., "Probes for Narcotic Receptor Mediated Phenomena. 11. Synthesis of 17-Methyl- and 17-Cyclopropylmethyl-3, 14-Dihydroxy-4,5α-Epoxy-6β-Fluoromorphinans (FOXY and CYCLOFOXY) as models of Opioid Ligands suitable for Positron Emission Transaxial Tomography." Heterocycles, vol. 23, 1985, pp. 99-106.
Brine, et al., "Ring C Conformation of 6β-Naltrexol and 6α-Naltrexol. Evidence from Proton and Carbon-13 Nuclear Magnetic Resonance[1]" Journal of Organic Chemistry, vol. 41, No. 21, 1976, pp. 3445-3448.
Olsen, et al., "Conjugate Addition Ligands of Opioid Antagonists. Methacrylate Esters and Ethers of 6α- and 6β-Naltrexol", J. Med. Chem., 1990, vol. 33, pp. 737-741.
Lutz, et al., "Reduction Studies in the Morphine Series. IX. Hydroxycodeinone." Journal of Organic Chemistry, vol. 4, 1939, pp. 220-233.
Goto, et al., "Formation of (+) Dihydrocodeine and (+) Dihydromorphine from Sinomenine." Proceedings of the Imperial Academy (Tokyo). 1940, vol. 16 pp. 403-404.
Goto, et al. "(+)-Dihydrocodein and (+) Dihydromorphin aus Sinomenin." Justus Liebigs Annalen der Chemie. 1941, vol. 547, pp. 194-200 (cumulative).

*Primary Examiner* — Charanjit Aulakh
(74) *Attorney, Agent, or Firm* — Kiera K. Mathey

(57) ABSTRACT

The present invention provides a process whereby morphinan-6-ones can be converted stereospecifically to the corresponding morphinan-6α-ols by catalytic hydrogenation under basic conditions.

33 Claims, No Drawings

US 8,236,957 B2

PROCESS FOR MAKING MORPHINAN-6α-OLS

CROSS-REFERENCE TO RELATED APPLICATIONS

This application claims priority from U.S. Provisional Application Ser. No. 61/188,574 filed Aug. 11, 2008, the contents of each of which are hereby incorporated by reference in their entirety.

FIELD OF THE INVENTION

This invention relates to a process for the manufacture of morphinan-6α-ols stereo-specifically and in high chemical yield by catalytic hydrogenation of the corresponding morphinan-6-ones under alkaline conditions.

BACKGROUND OF THE INVENTION

Morphinan-6α-ols, including such compounds as dihydrocodeine, oxymorphol, oxycodol and nalbuphine are important morphine derivatives due to their behaviour as potent analgesics or antagonists. Some prior synthetic routes to these compounds include;

from codeine or morphine, where the 6α-stereochemistry of the 6-hydroxy morphinan was already fixed by the stereo-chemistry of the natural product (see for example U.S. Pat. No. 6,887,999 for the hydrogenation of codeine to dihydrocodeine), Reduction of the 7,8-didehydro derivatives morphinan-6-ones using metal hydride reducing agents (e.g. sodium borohydride, lithium tri-sec-butyl borohydride) followed by hydrogenation to give the pure 6α-isomer of the corresponding morphinan-6-ol. (Sargent et al., "Hydroxylated codeine derivatives", Journal of Organic Chemistry, 23, 1247-1251, (1958), and A. C. Currie et al., J. Chem. Soc., 1960, 773.) This strategy was also used to convert 14-hydroxynormorphinones preferably to the 6α-epimer of the corresponding 14-hydroxydihydromorphine (preferably N—$O^3$-bis(ethoxycarbonyl)-14-hydroxynormorphinone to N—$O^3$-bis(ethoxycarbonyl)-14-hydroxydihydronormorphine; Kavka, "Preparation of nalbuphine having low levels of β-epimer", U.S. Pat. No. 5,756,745). Similarly, Cheng et al. converted methoxymethyl-protected naloxone to the corresponding 6-α epimer using potassium and sodium tri-sec-butylborohydride (Na and K-selectride respectively), sodium triethylborohydride and sodium triacetoxyborohydride in high chemical yield and >99% selectivity for the α-epimer (Stereoselective reduction of a morphinone, WO 2007/121114). U.S. Pat. Nos. 5,208,338 and 5,336,483 describe the preparation of radiolabeled N-substituted-6-iodo-3, 14-dihydroxy-4,5-α-epoxymorphinans (Scheme 4) which includes the selective reduction of the 6-carbonyl group using K-selectride, specifically described for the synthesis of 6α-naltrexol from naltrexone. TLC measurements indicated the absence of the epimeric 6β-isomer.

By contrast, reduction of oxymorphone (the morphinan-6-one saturated at the 7,8 position) using sodium borohydride promoted formation of the 6α morphinan-6-ol contaminated with significant amounts of the 6β isomer. (Burke and Rice., "Probes for narcotic receptor mediated phenomena. 11. Synthesis of 17-methyl- and 17-cyclopropylmethyl-3,14-dihydroxy-4,5α-epoxy-6β-fluoromorphinans (FOXY and CYCLOFOXY) as models of opioid ligands suitable for positron emission transaxial tomography." Heterocycles, 23, 1985, 99-106.)

Similarly, lithium aluminum hydride or sodium borohydride reduction of 8,14-dihydroxydihydrocodeinone (oxycodone) leads to epimeric dihydroxydihydrocodeines(oxycodols) (Sargent et al., "Hydroxylated codeine derivatives", Journal of Organic Chemistry, 23, 1247-1251, (1958)).

Similarly, reduction of naltrexone with either sodium borohydride in tetrahydrofuran or lithium tri-sec-butylborohydride in tetrahydrofuran at −78° C. gave 6α-naltrexol contaminated with traces of the 6β epimer. (Brine et al., "Ring C conformation of 6β-naltrexol and 6α-naltrexol. Evidence from Proton and Carbon-13 nuclear magnetic resonance." Journal of Organic Chemistry, 41, (1976) 3445-3448.)

Other literature report the reduction of naltrexone to 6α-naltrexol, e.g. L. D. Olsen et al., J. Med. Chem., 1990, 33, 737-741 or the reduction of 3-O-tert-butyldimethylsilyl protected naltrexone to the corresponding alpha isomer (G. A. Brine et al., J. Org. Chem., 1976, 41(21), 3445-3448) by using L-selectride in THF at −78° C. Traces of the beta isomer formed during the reduction were removed by chromatography or recrystallization.

The main drawbacks of the aforementioned procedures from the literature are low selectivities of the reductions (formation of 5-10% beta-isomer) resulting in a tedious procedure for the removal of the contaminant. Such removal requires either several recrystallizations giving an unacceptable loss of yield or a purification by column chromatography, which is not a commercially viable procedure. In case of the preparation of 6α-naltrexol from naltrexone, L-selectride was used as reducing agent at very low temperatures of −78° C., or 3-O-tert-butyldimethylsilyl protected naltrexone was used, making the process more complicated and expensive due to the need for special refrigerating equipment and/or expensive protecting groups.

In contrast to the metal hydride reducing agents traditionally used for the reduction of ketones to alcohols, hydrogenation does not require very low temperatures, or prior protection of the 3-hydroxy group, followed by de-protection to the desired 3-hydroxy-6α-morphinol and is operationally simpler and creates little or no waste during the processing. Few examples exist for the hydrogenation of the ketone group of morphinan-6-ones.

Hydrogenation of dihydrohydroxycodeinone (also known as oxycodone) in 10% aqueous acetic acid as solvent and platinum oxide as catalyst gave a mixture of 6α- and 6β-epimers of oxycodol with the 6α-epimer being the major product (Lutz R. E., and Small L., "Reduction studies in the morphine series. X. Hydroxycodeinone." Journal of Organic Chemistry, 4, 220-233, (1939)). In this solvent mixture the reaction clearly was not stereoselective.

There is only one example of a hydrogenation of a morphinan-6-one to a morphinan-6-ol. Hydrocodone was hydrogenated in ethanol as solvent using platinum oxide as catalyst (Grew and Powles, "Manufacture of 1-Dihydrocodeine" U.S. Pat. No. 3,830,819). The epimeric purity of the morphin-6-ol product was not mentioned in this example.

There remains a need for an efficient stereo-selective and environmentally friendly route to the pure 6α-epimer of morphinan-6-ols, particularly 14-hydroxymorphinan-ols. Increasingly, morphinan-6-ones and 14-hydroxymorphinan-6-ones are being used as intermediates in the synthesis of the corresponding morphinan-6-ols because they are available conveniently and in high yield from opiate raw materials thebaine and oripavine, both of which became commercially available in large quantities only relatively recently.

SUMMARY OF THE INVENTION

The present invention is drawn to a process for producing a morphinan-6α-ol compound of formula (IIa)

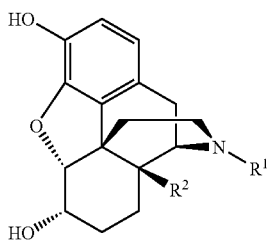

and pharmaceutically acceptable salts thereof,
comprising hydrogenating a morphinan-6-one compound of formula (I)

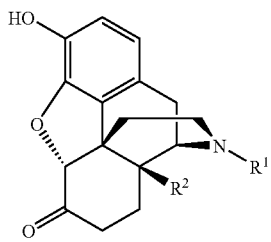

in an aqueous solvent and a water soluble base wherein the aqueous solvent is selected from the group consisting of water and a mixture of water and a water-miscible co-solvent in the presence of a catalyst at a pH between about 8.5 and about 14 (preferably, between about 11 and about 14, more preferably, between about 12.0 and about 13.5) to provide the compound of formula (IIa) having less than one percent of a morphinan-6β-ol compound of formula (IIb)

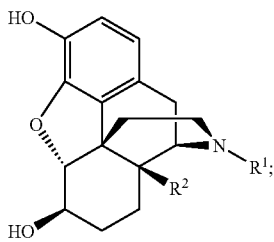

wherein
$R^1$ is selected from hydrogen, $C_1$-$C_{10}$ alkyl, $C_3$-$C_6$ cycloalkyl$C_1$-$C_{10}$ alkyl, —C(O)—$C_1$-$C_{10}$alkyl or —C(O)—O$C_1$-$C_{10}$alkyl; and
$R^2$ is selected from H, $OR^3$ or $OC(O)R^3$ wherein $R^3$ is selected from hydrogen or $C_1$-$C_{10}$ alkyl.
One embodiment of the present invention is the process wherein the catalyst is platinum; preferably, platinum oxide.

Another embodiment of the invention is the process wherein $R^1$ is selected from H,
$C_1$-$C_6$ alkyl, or $C_3$-$C_6$ cycloalkyl$C_1$-$C_6$ alkyl. Preferably, $R^1$ is selected from hydrogen, methyl, ethyl, propyl

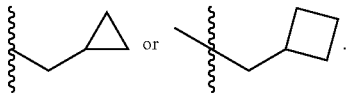

Illustrative of the invention is the process wherein the amount of the morphinan-6β-ol compound of formula (IIb) is less than 0.5 per cent, preferably, less than 0.20%, more preferably, less than 0.10% and most preferably, less than 0.05%.

Exemplifying the invention is the process wherein the compound of formula (I) is selected from the group consisting of hydromorphone, oxymorphone, norhydromorphone, noroxymorphone, naltrexone and nalbuphone.

Illustrating the invention is the process wherein the compound of formula (IIa) is selected from the group consisting of 6α-7,8-dihydromorphine, 6α-oxymorphol, 6α-norhydromorphol, 6α-noroxymorphol, 6α-naltrexol and 6α-nalbuphine. In a preferred embodiment, the compound of formula (IIa) is 6α-noroxymorphol or 6α-nalbuphine, most preferably, 6α-nalbuphine.

Further exemplifying the invention is the process wherein the hydrogenation is performed with a hydrogen donor selected from the group consisting of hydrogen gas, formic acid, sodium hypophosphite, and combinations thereof. Preferably, the hydrogen donor is hydrogen gas.

An illustration of the invention is the process wherein the aqueous solvent is water or water mixed with a water-miscible co-solvent selected from a $C_1$ to $C_4$ alcohol, dimethylformamide, dimethylacetamide, N-methylpyrrolidone or tetrahydrofuran. Preferably, the aqueous solvent is water or water mixed with a $C_1$ to $C_4$ alcohol, most preferably, the aqueous solvent is water or water mixed with 2-propanol.

Another illustration of the invention is the process wherein the water soluble base is selected from sodium hydroxide, potassium hydroxide, lithium hydroxide, caesium hydroxide or ammonium hydroxide. Preferably, the base is selected from sodium hydroxide or potassium hydroxide.

Further illustrating the invention is the process wherein the compound of formula (IIa) is 6α-noroxymorphol which further comprises the step of reacting the 6α-noroxymorphol with 3-bromo-1-propene to provide 6α-naloxol. This process for making 6α-naloxol may further comprise the step of isolating the 6α-naloxol.

In another embodiment of the present invention is a process for preparing 6α-naloxol of formula III

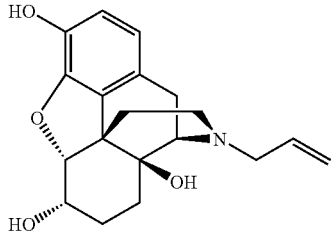

and pharmaceutically acceptable salts thereof, comprising hydrogenating a compound of formula (Ia)

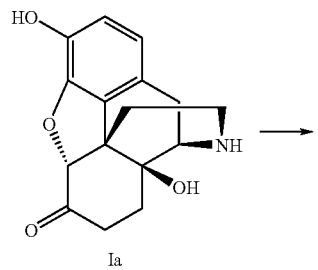

Ia

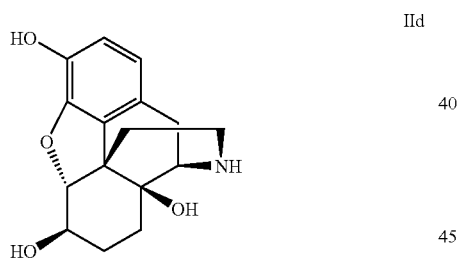

IIc in an aqueous solvent and a water soluble base wherein the aqueous solvent is selected from the group consisting of water and a mixture of water and a water-miscible co-solvent in the presence of a catalyst at a pH between about 8.5 and about 14 (preferably, between about 11 and about 14, more preferably, between about 12.0 and about 13.5) to provide a compound of formula (IIc) having less than one percent (preferably less than 0.5 per cent, more preferably, less than 0.20%, still more preferably, less than 0.10% and most preferably, less than 0.05%) of a morphinan-6β-ol compound of formula (IId)

IId and reacting the compound IIc with 3-bromo-1-propene to provide 6α-naloxol of formula III.

Further illustrating the invention is the process for making 6α-naloxol wherein the catalyst is platinum. Preferably, the catalyst is platinum oxide.

An illustration of the invention is the process for making 6α-naloxol wherein the hydrogenation is performed with a hydrogen donor selected from the group consisting of hydrogen gas, formic acid, sodium hypophosphite, and combinations thereof. Preferably, the hydrogen donor is hydrogen gas.

An example of the invention is the process for making 6α-naloxol wherein the aqueous solvent is water or water mixed with a water-miscible co-solvent selected from a $C_1$ to $C_4$ alcohol, dimethylformamide, dimethylacetamide, N-methylpyrrolidone or tetrahydrofuran. Preferably, the aqueous solvent is water or water mixed with a $C_1$ to $C_4$ alcohol, most preferably, the aqueous solvent is water or water mixed with 2-propanol.

Another example of the invention is the process for making 6α-naloxol wherein the water soluble base is selected from sodium hydroxide, potassium hydroxide, lithium hydroxide, caesium hydroxide or ammonium hydroxide. Preferably, the water soluble base is selected from sodium hydroxide or potassium hydroxide.

DETAILED DESCRIPTION OF THE INVENTION

The present invention provides a method for the conversion of a morphinan-6-one to a morphinan-6-ol wherein the 6α-epimer of the morphinan-6-ol is produced with only very small amount of the 6β-epimer present as an impurity as shown in Scheme 1, wherein $R^1$ and $R^2$ are as defined herein.

SCHEME 1

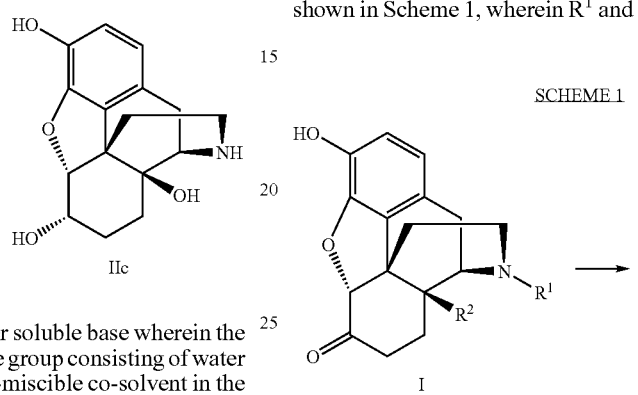

Thus, the present invention is directed to a method of producing a morphinan-6α-ol compound of formula (IIa)

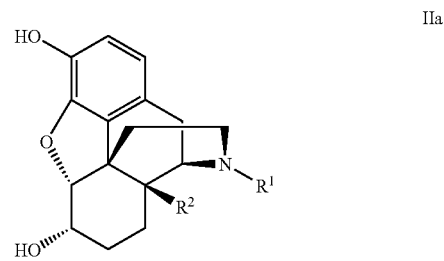

IIa and pharmaceutically acceptable salts thereof, comprising hydrogenating a morphinan-6-one compound of formula (I)

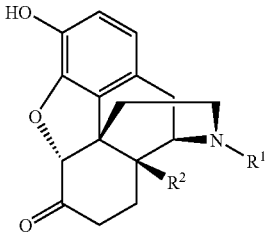

in an aqueous solvent and a water soluble base wherein the aqueous solvent is selected from the group consisting of water and a mixture of water and a water-miscible co-solvent in the presence of a catalyst at a pH between about 8.5 and about 14 to provide the compound of formula (IIa) having less than one percent of a morphinan-6β-ol compound of formula (IIb)

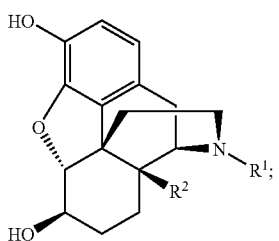

wherein $R^1$ is selected from hydrogen, $C_1$-$C_{10}$ alkyl, $C_3$-$C_6$ cycloalkyl$C_1$-$C_{10}$ alkyl (e.g., cyclopropylmethyl, cyclobutylmethyl), —C(O)—$C_1$-$C_{10}$alkyl or —C(O)—O$C_1$-$C_{10}$alkyl; preferably $R^1$ is selected from hydrogen, methyl,

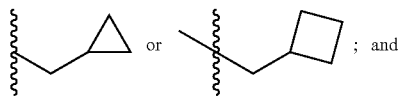

$R^2$ is selected from H, $OR^3$ or $OC(O)R^3$ wherein $R^3$ is selected from hydrogen or $C_1$-$C_{10}$ alkyl.

In accordance with the present invention, the conversion of a morphinan-6-one to a morphinan-6-ol can be achieved in a number of ways. The morphinan-6-one, particularly 3-hydroxymorphinan-6-ones can be dissolved in aqueous base at temperatures from about 0 to about 100° C. The solvent of choice is water either alone or mixed with any water miscible co-solvent inert to hydrogenation and readily apparent to one of ordinary skill in the art. Examples of water miscible co-solvents which can be used in the process of the present invention include, but are not limited to, $C_1$ to $C_4$ alcohols, dimethylformamide (DMF), dimethylacetamide, N-methylpyrrolidone, and tetrahydrofuran, with the preferred co-solvent being a $C_1$ to $C_4$ alcohol, most preferably, 2-propanol.

The base can be chosen from the Group 1 metal (lithium, sodium, potassium, cesium) hydroxides or ammonium hydroxide, preferably sodium hydroxide or potassium hydroxide. The pH of the reaction mixture may be maintained at from pH about 8.5 to about 14. In a preferred embodiment, the pH is maintained at a pH between about 11 and about 14, preferably, between about 12.0 and about 13.5, more preferably, between about 12.5 and about 13.5.

Suitable hydrogenation reagents are well known to those skilled in the art and typically include a hydrogenation catalyst and either hydrogen or a hydrogen transfer reagent such as sodium hypophosphite. Preferred hydrogenation catalysts are metal catalysts such as nickel, palladium, rhodium, or platinum either alone or dispersed on a support such as carbon or barium sulfate. The preferred catalyst is unsupported platinum oxide at a weight/weight (w/w) ratio relative to the 3-hydroxymorphinan-6-one from about 0.01% to about 10%, preferably about 1% w/w. In a preferred embodiment, hydrogen is then passed through the mixture at about 5 psi (80 kPa) or more. The hydrogenation step is carried out at a temperature from about 0 to about 100° C., preferably ambient temperature (25° C.). The temperature should be sufficient to dissolve the solids in the mixture, thereby providing a solution. The mixture is exposed to the hydrogenation reagents for at least about 1 hour and up to about 24 hours, preferably from about 3 to about 10 hours.

Upon completion, hydrogenation catalysts may be removed by filtration. If precious metal catalysts are used in the hydrogenation step, it is possible that unacceptable levels of metals remain in the final product (desirably, the level of heavy metals in the final product is <20 ppm). In one embodiment of the present invention, the solution of morphinan-6α-ol is subjected to a further process wherein the mixture is subjected to an activated carbon treatment. Suitably the mixture is stirred with activated carbon from about 15 minutes to about 5 hours at ambient temperature to about 100° C., preferably at about 50 to about 70° C. The hot mixture is then filtered to remove the carbon. Adjusting the pH to about 8.0 to about 10, preferably about 8.5 to about 10, more preferably, to about 10, and cooling the mixture to crystallize the product. The product is then collected by filtration. Suitably, the weight ratio of morphinan-6α-ol to activated carbon is from about 1:1 to about 40:1, preferably from about 10:1 to about 20:1.

The inventors of this new process found that platinum oxide catalyzed hydrogenations of morphinan-6-ones, particularly 14-hydroxy-morphinan-6-ones, gives the pure 6α-epimer of the corresponding morphinan-6-ol when a predominantly aqueous solvent with a water-soluble base is used. Use of aqueous base is particularly advantageous for the 3-hydroxymorphinan-6-one series, as the phenolic morphinans are readily soluble in aqueous base. Furthermore, adjusting the pH of the hydrogenation mixture to 12.0-13.5 is advantageous for the reaction rate and the selectivity of the hydrogenation to provide the α-epimer.

The resulting morphinan-6α-ol has very low levels (<1.0%) of the 6β-epimer and are advantageously incorporated into pharmaceutical products.

Compounds of formula (II) wherein $R^1$ is hydrogen may be further derivatized by one of ordinary skill in the art using known methods. For example, such compounds of formula (IIa) wherein $R^1$ is hydrogen (e.g., 6α-noroxymorphol) may be reacted with $C_3$-$C_{10}$ alkenyl halides (e.g., 3-bromo-1-propene) to provide compounds of formula (II) wherein $R^1$ is $C_3$-$C_{10}$ alkenyl (e.g., propenyl) such as 6α-naloxol. Similarly, 6α-noroxymorphol can be reacted with $C_1$-$C_{10}$ alkyl halides such as methyl bromide, or with $C_3$-$C_6$ cycloalkyl$C_1$-$C_{10}$ alkyl halides such as cyclopropylmethyl bromide and cyclobutylmethyl bromide to provide alternative processes for preparing compounds such as 6(α)-oxymorphol, 6α-naltrexol and 6α-nalbuphine, respectively.

More particularly, 6α-Naloxol can be prepared from 6α-Noroxymorphol by warming 6α-noroxymorphol (prepared as shown in Example 1) with 1.0-1.5 equivalents of 3-bromo-1-propene and 1.0-1.5 equivalents of sodium hydrogen carbonate in either dimethylformamide or N-methylpyrrolidinone as solvent at 45-90° C. for 2-24 hours. The crude product is isolated by adding water, adjusting the pH to 8.5-9.0 with ammonia and filtering. The crude product can be purified by re-crystallization to provide 6α-Naloxol.

The following Examples are set forth to aid in the understanding of the invention, and are not intended and should not be construed to limit in any way the invention set forth in the claims which follow thereafter.

EXAMPLE 1

Conversion of Noroxymorphone to Noroxymorphol(14-Hydroxydihydronormorphine)

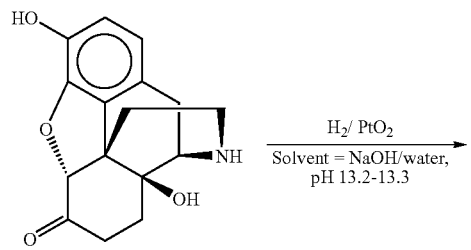

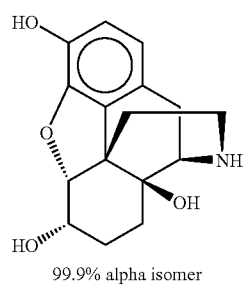

99.9% alpha isomer

Noroxymorphone (5 g) was suspended in water (75 ml). The pH was adjusted to 13.3 with aqueous solution of NaOH (40% weight/volume (w/v)). The solution was warmed to 50° C. and aged with stirring until complete dissolution was observed. To this solution was added Adams catalyst ($PtO_2$, 50 mg) and the mixture was hydrogenated at 40 psi at room temperature for 3.5 h with 1200 rpm agitation speed. The catalyst was then removed with 5 ml water rinse. The pH was adjusted to 9.1 with glacial acetic acid and the resulting suspension was aged for 1 h. The suspension was filtered with a small volume of water rinse. The solid was dried at 60° C. under vacuum for 5 h (3.80 g, 76% yield by weight, overall yield/accountability was estimated to be approximately 90% taking into account the aliquots taken for sampling and the material lost to the mother liquor). The solid isolated was characterised to be 6(α)-noroxymorphol(14-hydroxydihydronormorphine). The level of β-isomer was 0.12% by HPLC analysis (Example 9, Method A).

EXAMPLE 2

Conversion of Oxymorphone to Oxymorphol(14-Hydroxydihydromorphine)

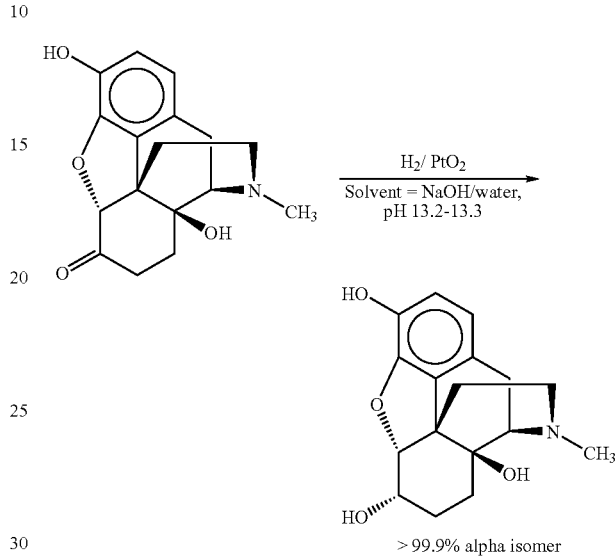

> 99.9% alpha isomer

Oxymorphone (5 g, assay=84.7%) was suspended in water (200 ml). The pH was adjusted to 13.2 with aqueous solution of NaOH (40% w/v). The solution was warmed to ~50° C. and aged with stirring until complete dissolution was observed. To this solution was added Adams catalyst ($PtO_2$, 50 mg) and the mixture was hydrogenated at 40 psi at room temperature for 9 h with 1200 rpm agitation speed. The catalyst was then removed with 5 ml water rinse. The pH was adjusted to 9.1 with glacial acetic acid. No precipitation was observed. The solution was then concentrated in vacuo at 65° C. to a volume of approximately 75 ml. The resulting suspension was cooled to room temperature, aged for 1 h and filtered with 5 ml water rinse. The solid was dried at 60° C. under vacuum for 4 h (3.45 g, 82% yield by weight). The solid was characterised to be 6(α)-oxymorphol(14-hydroxydihydromorphine). The β-isomer was at 0.02% by HPLC analysis (Example 9, Method A).

EXAMPLE 3

Conversion of Nalbuphone to Nalbuphine

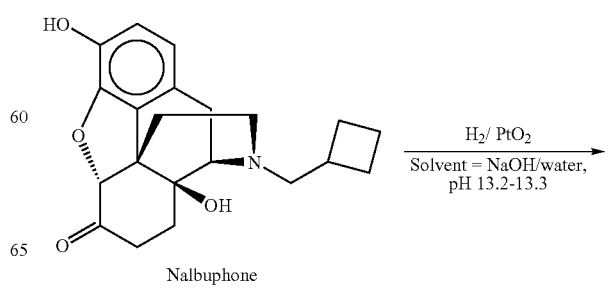

Nalbuphone

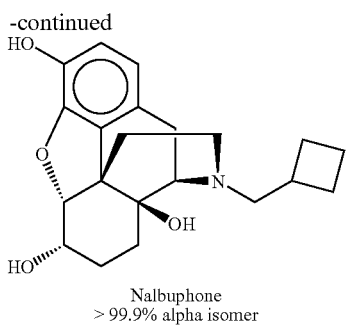

Nalbuphone
> 99.9% alpha isomer

A 500 ml three necked round bottom flask was charged with crude Nalbuphone Hydrochloride (50 grams, 93.14 mmol), sodium acetate (0.77 grams, 9.31 mmol), activated charcoal (2 grams, Norit CAP Super) and water (300 mL). Subsequently, the mixture was heated (batch temperature of 80° C.) under reduced pressure (p=250 mbar). A total amount of 16.7 g distillate was collected at an internal temperature of 55-65° C. during 40 minutes. The vacuum supply was then removed and the mixture stirred at a temperature of 65° C. for 1 hour. Subsequently, the mixture was filtered through a 2 cm pad of diatomaceous earth (Celite) and the filter cake rinsed with water (two 15 mL aliquots) to give: 359.5 g of a yellow solution containing 89.1 mg/g=32.02 g=90.1 mmol=96.7% nalbuphone (as the hydrochloride salt).

A 1 liter round bottom flask was charged with sodium hydroxide solution (30%, 24.8 grams, 186.3 mmol) and 2-propanol (160 mL). The above solution of Nalbuphone Hydrochloride was poured to the stirred mixture of aqueous sodium hydroxide and 2-propanol. The pH of the obtained golden solution was found to be 11.8 and was adjusted to 12.7 by adding an additional amount of 30% aqueous sodium hydroxide. The solution was distributed between two 500 ml Parr hydrogenation flasks. After inerting with argon, platinum oxide catalyst (0.561 gram, 2.33 mmol) and activated charcoal (Norit CAP Super, 1.0 gram) were added and the mixtures hydrogenated at 40-50 pounds/square inch (psi) at room temperature in a Parr shaker.

| time | conversion flask A | conversion flask B | remarks |
|---|---|---|---|
| 2 h | 99.6% | 90.6% | precipitate in B |
| 4 h | 99.6% | 93.4% | precipitate in A + B |
| 6 h | — | 99.8% | |

(after 4 hours, the precipitate in flask B was dissolved by heating to 40° C.). Both flasks were then heated to an internal temperature of 35° C. to ensure complete dissolution of the product and then filtered over a 2 cm pad of celite. The filter cake was rinsed with water (two 15 ml aliquots) to give 569 grams of a copper-colored solution containing 55.35 mg/g=31.49 g=94.6% nalbuphine. The solution was treated with aqueous ammonia solution (25% 1.4 g) and thereafter the pH was adjusted to 9.1-9.2 by adding acetic acid. At a pH of about 10, the mixture was seeded with some crystals of Nalbuphine. The beige slurry was then stirred for 1 hour at room temperature and then the product was filtered off and washed with $H_2O$ to give: 44.0 g of crude, wet nalbuphine (purity=98.7%) and 627 g mother liquor (golden) containing: 0.65 mg/g=0.41 g=1.2% yield.

The crude wet product was charged together with methanol (100 ml) in a 250 ml three necked flask and heated to reflux for 15 minutes and then cooled slowly (over night in the hot oil bath) to room temperature. After stirring another 2 hours at 0-5° C., the product was isolated by filtration. The wet product was rinsed with methanol (two 15 ml aliquots) (wet product 36 g) and dried in the cabinet at 75° C. for 3 hours at a pressure of about 20 mbar to give 29.88 g (86.9%) of a light beige solid.

purity: 99.3%

Impurities

N-Cyclopentyl derivative: 0.08%

Nalbuphone: 0.10%,

β-isomer: 0.02%, (Example 9, Method A)

unknown ($t_R$=17.0'): 0.10%,

3(O)-cyclobutylmethyl nalbuphine: 0.22%,

3(O)-cyclobutylmethyl nalbuphine: 0.19%.

assay: 96.8%

EXAMPLE 4

A series of experiments were run according to the procedure in Example 3 with the exception of changing the pH of the reaction mixture. The effect of the change of pH on the stereo-selectivity (as determined by Example 9, Method A) and the rate of reaction is shown below.

| pH | Time | Ratio of α/β epimer (%) | Reaction completion (%) | |
|---|---|---|---|---|
| 11.0 | 2 hours | 99.55/0.45 | 83.55 | |
|  | 4.25 hours | 99.47/0.43 | 98.13 | |
| 11.5 | 2 hours | 99.78/0.22 | 90.68 | |
|  | 4.25 hours | 99.86/0.14 | 99.73 | |
| 12.0 | 2 hours | 99.88/0.12 | 95.60 | |
|  | 4.5 hours | 99.88/0.12 | 99.80 | |
|  |  |  | A | B |
| 12.7 | 2 hours |  | 99.6 | 90.6 |
| (from | 4 hours |  | 99.6 | 93.4 |
| Example 3 above) | 6 hours | 99.98/0.02 | — | 99.8 |

EXAMPLE 5

Conversion of Naltrexone to Naltrexol

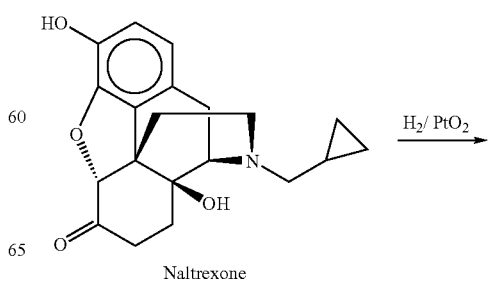

Naltrexone

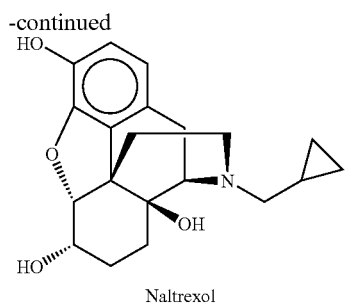

Naltrexol

Crude naltrexone hydrochloride (25.0 g) was dissolved in deionized water ("DIW") (200 mL). The pH was adjusted from 2.1 to 13.1 by dropwise addition of 40% $NaOH_{(aq)}$ to the stirred solution. (note: precipitate formed at pH~8 and re-dissolved at pH~12). Platinum oxide catalyst (200 mg) was added and the mixture hydrogenated with stirring (Parr Hydrogenator: T=45° C.; $H_2$ pressure=45 psi; stirrer=1500 rpm) for 3 hours. The reaction mixture was filtered through Celite and the cake washed with DIW (20 mL). Isopropyl alcohol (20 mL) was added to the filtrate and the solution stirred and heated to 45° C. The pH of the solution was adjusted to 10.8 by dropwise addition of glacial acetic acid. The mixture was aged for 20 min. at 45° C. The pH was further adjusted to 8.8 by slow addition of glacial acetic acid (total volume added=5.5 mL). The stirred mixture was aged for 15 min. and then filtered. Solids were washed with DIW (2×10 mL) and dried overnight under vacuum at 60° C. to afford an off-white powder (mass=15.0 g). The product, naltrexol, was analysed by HPLC (Example 10, Method B): Purity $\%_{area}$=98.6.

EXAMPLE 6

A series of experiments were run under acidic conditions:

A) Experiment 1

1. Noroxymorphone (5 g) was dissolved in a mixture of water (100 ml) and concentrated sulfuric acid (~1.5 ml). The pH of solution was measured to be at 0.9.
2. The mixture was hydrogenated at 40° C.-100° C. and 40 psi using $PtO_2$ (50 mg) with an agitation speed of 1200 rpm.
3. After 5 h, no significant reaction was observed by HPLC analysis (Example 9, Method A).

B) Experiment 2

1. Oxymorphone (5 g) was dissolved in a mixture of water (75 ml) and concentrated sulfuric acid (~1.5 ml). The pH of solution was measured to be at 0.7.
2. The mixture was hydrogenated at 40° C.-65° C. and 40 psi using $PtO_2$ (50 mg) with an agitation speed of 1200 rpm.
3. After 5 h, no significant reaction was observed by HPLC analysis (Example 9, Method A).

C) Experiment 3

1. Noroxymorphone (21 g) was dissolved in a mixture of water (102 ml) and acetic acid (8 ml) at 50° C. The pH of the solution was measured to be at 4.2.
2. The solution was cooled to room temperature and $PtO_2$ (105 mg) was added.
3. The mixture was hydrogenated at 40 psi for 4 h and 45 min with an agitation speed of 1200 rpm.
4. After the initial 3 h into hydrogenation, only 21% conversion to α-noroxymorphol was seen by HPLC analysis. Temperature was increased to 45° C. for the remaining 1 h and 45 min. No further reaction was observed in this period.
5. The catalyst was removed by filtration with a water rinse (46 ml).
6. The filtrate was allowed to cool to room temperature and then fresh $PtO_2$ (100 mg) was added. The solution was further hydrogenated at 40 psi room temperature for 1 h with an agitation speed of 1200 rpm.
7. The solution was then kept under hydrogen without agitation for approximately 70 h.
8. The agitation was re-commenced and the mixture was hydrogenated for further 5 h using the conditions described in step 6.
9. After this time, the HPLC analysis (Example 9, Method A) showed that only 28% conversion to noroxymorphol took place. The epimeric purity was not examined.

EXAMPLE 7

Conversion of Noroxymorphol to Naloxol

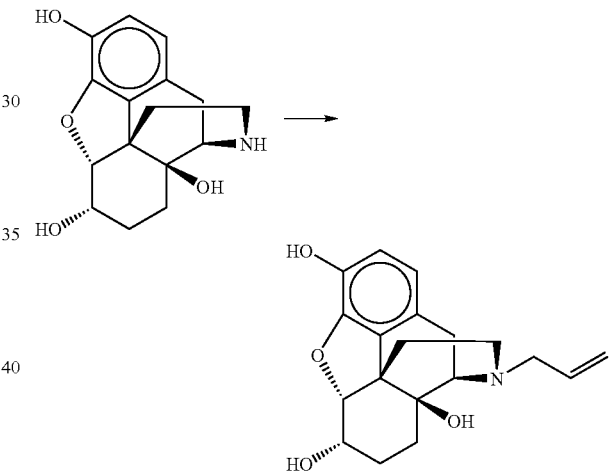

To a stirred mixture of noroxymorphol (4.75 g) and sodium bicarbonate (1.70 g) in N-methyl-2-pyrrolidone ("NMP") (11.0 mL) at 45° C. was added allyl bromide (2.2 mL) all at once. The mixture was stirred at 45° C. and reaction progress was monitored by HPLC. A further two aliquots of allyl bromide were added (0.12 eqv. at t=26 hrs and 0.14 eqv. at t=31 hrs) in order to drive the reaction to completion. The reaction was halted after 52 hours, however, HPLC analysis indicated that the reaction was complete after 46 hrs. Slight over-alkylation resulting in O-allylnaloxol (~2% by HPLC area) was indicated by HPLC analysis. Ethyl acetate (55 mL) was added to the reaction mixture which led to unwanted gum formation (a precipitate was desired). Aqueous sodium hydroxide solution (8% w/v; 50 mL) was added and the mixture transferred to a separatory funnel. A further 50 mL of $NaOH_{(aq)}$ (8% w/v) was added and the two layers mixed well before being separated. To the combined aqueous layer (100 mL) was added ethanol (20 mL). The pH of the aqueous ethanolic mixture was adjusted to 9.1 with glacial acetic acid at 35° C. The mixture was stirred at 35° C. for 30 min and then filtered. The collected solid was washed with 2×5 mL of DIW. The solid was dried under vacuum at 60° C. overnight to give a pale beige powder (3.69 g). The product, naloxol, was analysed by HPLC (Example 10, Method B): Purity %$_{area}$=99.36.

Solid (3.69 g) was mostly dissolved in a minimum of hot methanol (60 mL; 50° C.) and filtered. The filtrate was allowed to cool slowly to room temperature and then cooled overnight at 4° C. A white crystalline solid (2.3 g) was obtained by filtration, washing with cold methanol (10 mL, T=0° C.) followed by drying under vacuum overnight at 60° C. The product, purified naloxol, (beige crystalline solid) was analysed by HPLC (Example 10, Method B): Purity %$_{area}$=99.63.

EXAMPLE 8

Conversion of Noroxymorphol to Naltrexol

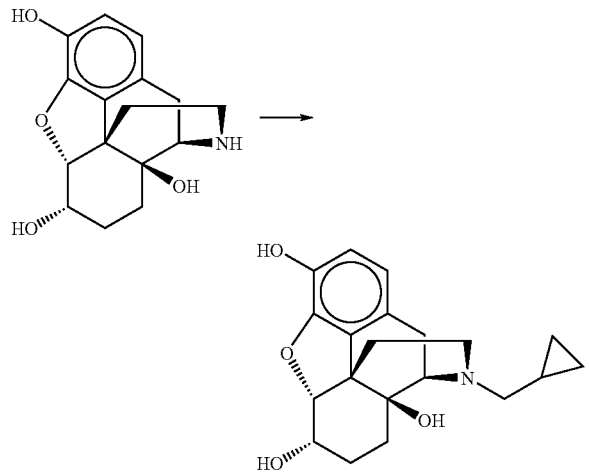

To a stirred mixture of noroxymorphol (4.80 g) and sodium bicarbonate (1.25 g) in NMP (11 mL) at 45° C. was added cyclopropylmethyl bromide ("CPMB") (2.4 mL) all at once. The mixture was stirred and slowly heated to 35° C. over 45 minutes. A thick precipitate formed. A further 5 mL of NMP was added and the mixture stirred and heated at 45° C. and reaction progress monitored by HPLC. A further 0.5 molar equivalents of CPMB was added at t=28 hrs. The reaction was halted after 74 hours, however, HPLC analysis indicated that the reaction was complete after 68 hrs. Slight over-alkylation resulting in O-allylnaltrexol (~2% by HPLC area) was indicated by HPLC analysis. Ethyl acetate (55 mL) was added to the reaction mixture with stirring. Solids were collected by filtration and washed with ethyl acetate (20 mL). The solid was dried under vacuum at 60° C. for 2 hrs to give a beige powder. The product, naltrexol, was analysed by HPLC (Example 10, Method B): Purity %$_{area}$=98.70.

To this solid (5.6 g) was added 22.5 mL of DIW followed by 5 mL of ethanol (initial pH=7.8). The pH of the stirred mixture was adjusted to 3.1 by dropwise addition of glacial acetic acid (~12 mL). A further 20 mL of DIW was added and the stirred mixture was heated to 60° C. (most of the material dissolved). The pH was then adjusted slowly to 8.8 with aqueous ammonia (28% w/v; ~25 mL). The mixture was aged for 1 hr at 55° C. The pH was further adjusted to 8.46 from 8.80 by adding a few drops of glacial acetic acid. The mixture was stirred at 55° C. for 10 min. and then filtered with water rinses (10 ml+5 ml). The product, purified naltrexol, was dried under vacuum overnight at 60° C. to give an off-white powder (mass=3.1 g). The solid was analysed by HPLC (Example 10, Method B): Purity %$_{area}$=99.59.

EXAMPLE 9

HPLC Method A

HPLC Method A was used to determine the purity of all of the Examples except for Examples 5, 7 and 8.

HPLC method for analysis of oxymorphone and related impurities at pH 10 using a Waters Xbridge™ Shield Phenyl column (Waters Corporation, Milford, Mass.).

Materials & Equipment:

| | |
|---|---|
| Potassium Formate | 99.995+% |
| Ammonia 28% | Reagent grade |
| Acetonitrile | HPLC grade |
| Methanol | HPLC grade |

Purified water—Milli-Q® water (Millipore Corporation, Billerica, Mass.)

Waters Xbridge™ Phenyl column, 150×3.0 mm, 3.5 μm

Testing Instructions:

Mobile Phase Instructions:

Line A—1.32±0.01 g of potassium formate was dissolved in 1L of Milli-Q® water and the pH of the buffer adjusted to 10.0 with ammonia 28%

Line B—acetonitrile

Line C—methanol (this solvent used for line storage only)

Line D—Milli-Q® water (1 day expiry)

Needle Wash—50% methanol/50% Milli-Q® water

Instrument Settings:

| Flow Rate | Oven Temp | Detector λ | Injection Volume | Vacuum Degassing | Run time |
|---|---|---|---|---|---|
| 0.65 mL/min | 40° C. | 284 nm | 5 μL | Continuous | 30 min |

Mobile Phase Composition:

| Time (min) | Line A | Line B | Line C | Line D | Curve |
|---|---|---|---|---|---|
| 0 | 95% | 5% | 0% | 0% | 1 |
| 2 | 95% | 5% | 0% | 0% | 1 |
| 26 | 60% | 40% | 0% | 0% | 6 |
| 30 | 95% | 5% | 0% | 0% | 1 |

The samples were injected and chromatographed along with standard reference samples. After the sample set was run by the HPLC, the peaks were identified by comparison with the standards that were run in the sample set.

The oxymorphol product formed in example 2 was analysed using this HPLC method. Retention times of oxymorphone, α-oxymorphol and β-oxymorphol on this method were 13.4, 12.9 and 12.1 min respectively, all confirmed by spiking experiments.

Since noroxymorphol elutes quite early on in this HPLC method, it was modified as follows for noroxymorphol. The buffer solution potassium formate was replaced with di-potassium hydrogen phosphate* but all other parameters remained the same. The retention times of noroxymorphone, α-noroxymorphol and β-noroxymorphol on this method were 7.6, 6.4 and 5.6 min respectively, all confirmed by spiking experiments.

Preparation of Hydrogen Phosphate Buffer Solution:

38.8 g of di-potassium hydrogen was added into 1000 ml of Mill-Q water and the pH adjusted to 6.2±0.05 with phosphoric acid after filtration.

EXAMPLE 10

HPLC Method B

The following HPLC Method B was used for Examples 5, 7 and 8.

Column: Alltima $C_8$, 150 mm×4.6 mm×3 μm
Flow Rate: 1.30 mL/min
Oven Temperature: 50° C.
λ: 230 nm
Injection Volume: 5 μL
Run Time: 46 min

| Line | Reagent: |
|---|---|
| A | 29 mL $H_3PO_4$ (85%) diluted to 1.00 L in MilliQ water |
| B | Acetonitrile |
| C | Methanol (not used) |
| D | MilliQ water |

| T/min | % A | % B | % D | curve |
|---|---|---|---|---|
| 0 | 10 | 0 | 90 | — |
| 5 | 10 | 3 | 87 | 6 |
| 10 | 10 | 10 | 80 | 6 |
| 20 | 10 | 10 | 80 | 6 |
| 35 | 10 | 90 | 0 | 6 |
| 38 | 10 | 90 | 0 | 6 |
| 46 | 10 | 0 | 90 | 1 |

The samples were injected and chromatographed along with standard reference samples. After the sample set was run by the HPLC, the peaks were identified by comparison with the standards that were run in the sample set.

One or more currently preferred embodiments have been described by way of example. It will be apparent to persons skilled in the art that a number of variations and modifications can be made without departing from the scope of the invention as defined in the claims.

What is claimed is:

1. A process for producing a morphinan-6α-ol compound of formula (IIa)

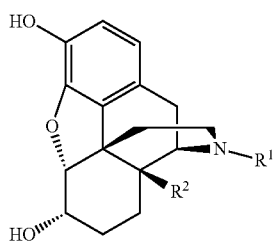

and pharmaceutically acceptable salts thereof,
comprising hydrogenating a morphinan-6-one compound of formula (I)

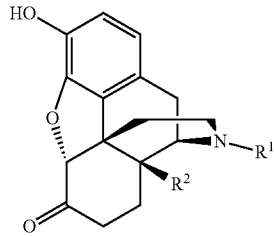

in an aqueous solvent and a water soluble base wherein the aqueous solvent is selected from the group consisting of water and a mixture of water and a water-miscible co-solvent in the presence of a catalyst wherein said catalyst is platinum or platinum oxide, at a pH between about 11 and about 14 to provide the compound of formula (IIa) having less than one percent of a morphinan-6β-ol compound of formula (IIb)

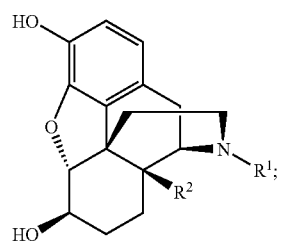

wherein
$R^1$ is selected from hydrogen, $C_1$-$C_{10}$ alkyl, $C_3$-$C_6$ cycloalkyl$C_1$-$C_{10}$ alkyl, —C(O)—$C_1$-$C_{10}$alkyl or —C(O)—O$C_1$-$C_{10}$alkyl; and
$R^2$ is selected from H, $OR^3$ or $OC(O)R^3$ wherein $R^3$ is selected from hydrogen or $C_1$-$C_{10}$ alkyl.

2. The process of claim 1, wherein the pH is between about 12.0 and about 13.5.

3. The process of claim 1, wherein $R^1$ is selected from H, $C_1$-$C_6$ alkyl, or $C_3$-$C_6$ cycloalkyl$C_1$-$C_6$ alkyl.

4. The process of claim 3, wherein $R^1$ is selected from hydrogen, methyl, ethyl, propyl,

5. The process of claim 1, wherein the amount of the morphinan-6β-ol compound of formula (IIb) is less than 0.5 percent.

6. The process of claim 1, wherein the compound of formula (I) is selected from the group consisting of hydromorphone, oxymorphone, norhydromorphone, noroxymorphone, naltrexone and nalbuphone.

7. The process of claim 1, wherein the compound of formula (IIa) is selected from the group consisting of 6α-7,8-dihydromorphine, 6α-oxymorphol, 6α-norhydromorphol, 6α-noroxymorphol, 6α-naltrexol and 6α-nalbuphine.

8. The process of claim 1 wherein the hydrogenation is performed with a hydrogen donor selected from the group consisting of hydrogen gas, formic acid, sodium hypophosphite, and combinations thereof.

9. The process of claim 8 wherein the hydrogen donor is hydrogen gas.

10. The process of claim 1, wherein the aqueous solvent is water or water mixed with a water-miscible co-solvent selected from a $C_1$ to $C_4$ alcohol, dimethylformamide, dimethylacetamide, N-methylpyrrolidone or tetrahydrofuran.

11. The process of claim 10 wherein the aqueous solvent is water or water mixed with a $C_1$ to $C_4$ alcohol.

12. The process of claim 11 wherein the aqueous solvent is water or water mixed with 2-propanol.

13. The process of claim 1 wherein the water soluble base is selected from sodium hydroxide, potassium hydroxide, lithium hydroxide, caesium hydroxide or ammonium hydroxide.

14. The process of claim 13 wherein the base is selected from sodium hydroxide or potassium hydroxide.

15. The process of claim 5, wherein the amount of the morphinan-6β-ol compound of formula (IIb) is less than 0.20%.

16. The process of claim 5, wherein the amount of the morphinan-6β-ol compound of formula (IIb) is less than 0.10%.

17. The process of claim 5, wherein the amount of the morphinan-6β-ol compound of formula (IIb) is less than 0.05%.

18. The process of claim 7, wherein the compound of formula (IIa) is 6α-noroxymorphol or 6α-nalbuphine.

19. The process of claim 18, wherein the compound of formula (IIa) is 6α-noroxymorphol and wherein the process further comprises the step of reacting the 6α-noroxymorphol with 3-bromo-1-propene to provide 6α-naloxol.

20. The process of claim 19 further comprising the step of isolating the 6α-naloxol.

21. A process for preparing 6α-naloxol of formula III

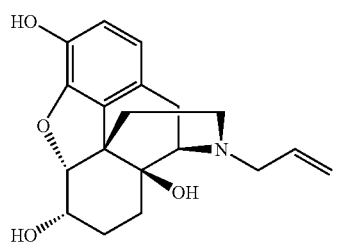

and pharmaceutically acceptable salts thereof, comprising hydrogenating a compound of formula (Ia)

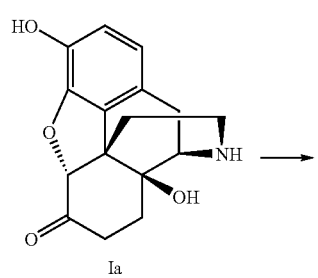

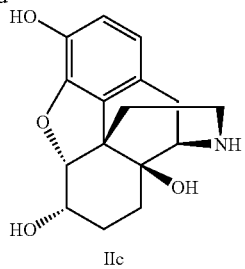

in an aqueous solvent and a water soluble base wherein the aqueous solvent is selected from the group consisting of water and a mixture of water and a water-miscible co-solvent in the presence of a catalyst wherein said catalyst is platinum or platinum oxide, at a pH between about 11 and about 14 to provide a compound of formula (IIc) having less than one percent of a morphinan-6β-ol compound of formula (IId)

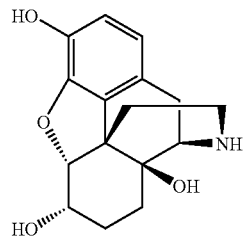

and reacting the compound IIc with 3-bromo-1-propene to provide 6α-naloxol of formula III.

22. The process of claim 21, wherein the pH is between about 12.0 and about 13.5.

23. The process of claim 22, wherein the amount of the morphinan-6β-ol compound of formula (IId) is less than 0.5 percent.

24. The process of claim 23 wherein the hydrogenation is performed with a hydrogen donor selected from the group consisting of hydrogen gas, formic acid, sodium hypophosphite, and combinations thereof.

25. The process of claim 24 wherein the hydrogen donor is hydrogen gas.

26. The process of claim 22, wherein the aqueous solvent is water or water mixed with a water-miscible co-solvent selected from a $C_1$ to $C_4$ alcohol, dimethylformamide, dimethylacetamide, N-methylpyrrolidone or tetrahydrofuran.

27. The process of claim 26 wherein the aqueous solvent is water or water mixed with a $C_1$ to $C_4$ alcohol.

28. The process of claim 27 wherein the aqueous solvent is water or water mixed with 2-propanol.

29. The process of claim 26 wherein the water soluble base is selected from sodium hydroxide, potassium hydroxide, lithium hydroxide, caesium hydroxide or ammonium hydroxide.

30. The process of claim 29 wherein the base is selected from sodium hydroxide or potassium hydroxide.

31. The process of claim 22, wherein the amount of the morphinan-6β-ol compound of formula (IId) is less than 0.20%.

32. The process of claim 22, wherein the amount of the morphinan-6β-ol compound of formula (IId) is less than 0.10%.

33. The process of claim 22, wherein the amount of the morphinan-6β-ol compound of formula (IId) is less than 0.05%.

* * * * *